United States Patent
Thyzel

(10) Patent No.: US 12,251,337 B2
(45) Date of Patent: Mar. 18, 2025

(54) EYE TREATMENT DEVICE, IN PARTICULAR FOR GLAUCOMA

(71) Applicant: A.R.C. Laser GmbH, Nuremberg (DE)

(72) Inventor: Reinhardt Thyzel, Eckental (DE)

(73) Assignee: A.R.C. Laser GmbH, Nuremberg (DE)

( * ) Notice: Subject to any disclaimer, the term of this patent is extended or adjusted under 35 U.S.C. 154(b) by 380 days.

(21) Appl. No.: 17/173,744

(22) Filed: Feb. 11, 2021

(65) Prior Publication Data
US 2022/0192884 A1 Jun. 23, 2022

(30) Foreign Application Priority Data
Dec. 22, 2020 (DE) ............ 10 2020 134 738.3

(51) Int. Cl.
- *A61F 9/00* (2006.01)
- *A61F 9/008* (2006.01)
- *A61F 9/009* (2006.01)

(52) U.S. Cl.
CPC .......... *A61F 9/00821* (2013.01); *A61F 9/009* (2013.01); *A61F 2009/00891* (2013.01); *A61F 2210/0071* (2013.01)

(58) Field of Classification Search
CPC ........ A61F 9/009; A61F 9/0079; A61F 9/008; A61F 2009/00865; A61F 2009/00868; A61F 2009/00872; A61F 2009/00874; A61F 2009/00876; A61F 2009/00891
See application file for complete search history.

(56) References Cited

U.S. PATENT DOCUMENTS

| | | | | |
|---|---|---|---|---|
| 4,054,744 | A * | 10/1977 | Beaman | H01G 4/236 73/304 C |
| 5,372,595 | A * | 12/1994 | Gaasterland | A61F 9/008 606/4 |
| 8,586,897 | B2 * | 11/2013 | Cronin | H05B 6/80 219/690 |
| 8,945,103 | B2 * | 2/2015 | Chew | A61F 9/008 606/6 |
| 9,700,461 | B2 * | 7/2017 | Buzawa | A61F 9/008 |
| 10,292,868 | B2 * | 5/2019 | Chew | A61F 9/00821 |
| 10,758,118 | B2 * | 9/2020 | Chen | B23K 26/0096 |
| 11,576,569 | B2 * | 2/2023 | Chen | A61B 18/22 |
| 2013/0144281 | A1 * | 6/2013 | Lewinsky | A61B 18/20 606/16 |
| 2015/0374539 | A1 * | 12/2015 | Buzawa | A61F 9/00781 606/4 |

(Continued)

FOREIGN PATENT DOCUMENTS

DE 102017104673 A1 9/2018

OTHER PUBLICATIONS

Kobykgno et al. "Multiblock Copoly(Urethane-Amide-Imide)s With the Properties of Thermoplastic Elastomers" Materials Physics and Mechanics 40 (2018) 221-230, May 14, 2018 (Year: 2018).*

*Primary Examiner* — Shirley X Jian
(74) *Attorney, Agent, or Firm* — Workman Nydegger

(57) ABSTRACT

An eye treatment device, in particular for use in glaucoma therapy, comprising a least one applicator head for applying laser light (L) into the eye, said applicator head comprising at least one light guide having an exit end for the laser light (L) and a cavity having an opening enclosed by a contact ring for placement on the eye, said light guide extending self-supporting and/or exposed within the cavity.

17 Claims, 4 Drawing Sheets

(56) References Cited

U.S. PATENT DOCUMENTS

| | | | |
|---|---|---|---|
| 2016/0095507 A1* | 4/2016 | Uram | A61B 1/07 |
| | | | 600/108 |
| 2018/0000337 A1* | 1/2018 | Chen | A61B 18/22 |
| 2019/0117455 A1* | 4/2019 | Garcia | A61F 9/00754 |
| 2021/0186755 A1* | 6/2021 | Khoo | A61F 9/008 |
| 2022/0192884 A1* | 6/2022 | Thyzel | A61F 9/009 |

* cited by examiner

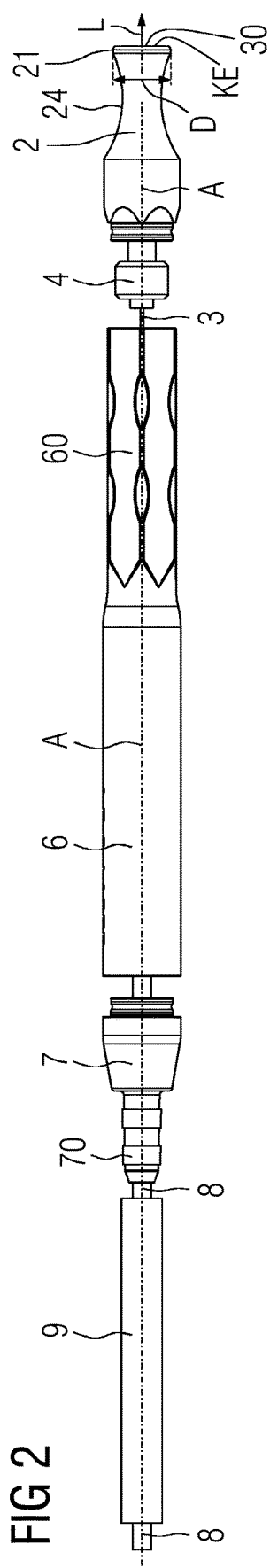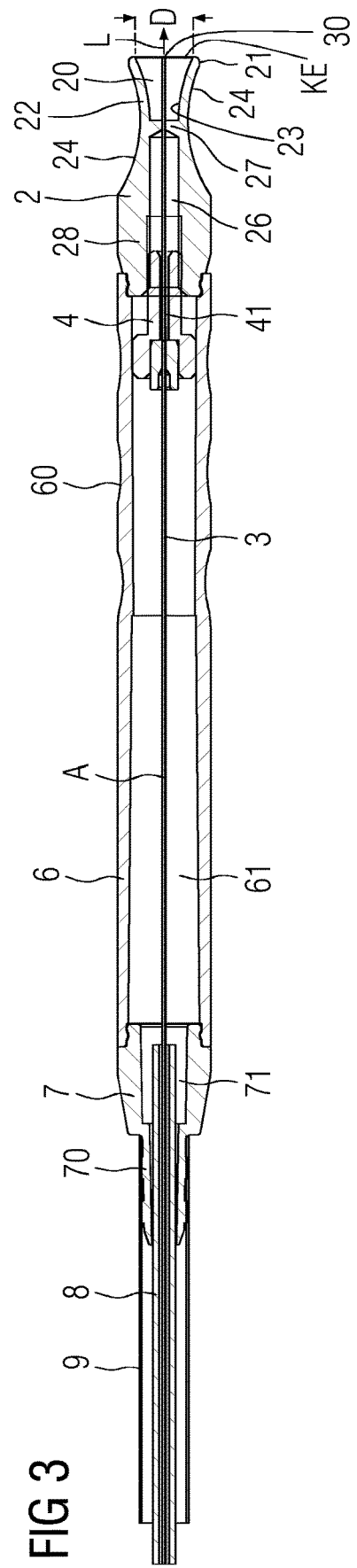

EYE TREATMENT DEVICE, IN PARTICULAR FOR GLAUCOMA

CROSS-REFERENCE TO RELATED APPLICATIONS

The present invention claims the benefit of priority to German Patent Application No. DE 10 2020 134 738.3, filed Dec. 22, 2020, entitled "Augenbehandlungsvorrichtung, Insbesondere Für Glaukome," the entire content of which is incorporated herein by reference.

BACKGROUND OF THE INVENTION

1. Field of the Invention

The invention relates to an eye treatment device, in particular for use in the treatment or therapy of glaucoma.

2. The Relevant Technology

Glaucoma is a serious eye disease that threatens partial or complete blindness due to damage to the retina. A common cause of glaucoma is increased intraocular pressure. Such an increased intraocular pressure can occur, for example, if the flow channel for the eye fluid is narrowed in the area of the ciliary muscles and the trabecular meshwork or if there is too much eye fluid without corresponding pressure equalisation.

Eye treatment devices are known by which the flow channel is widened again and/or the ciliary muscle is partially destroyed by means of laser light irradiated through the cornea, thereby reducing the ocular fluid or the intraocular pressure, for example by so-called cyclo photocoagulation using laser light of high power from the infrared spectrum, in particular 810 nm.

EP 3 160 379 B1 discloses a treatment probe for treating a portion of the eye comprising an elongate body defining a handle having a proximal end and a distal end, and a solid contact member connected to the distal end of the elongate body. The contact element comprises a convex contact surface for contacting the surface of the eye. The probe further comprises a treatment fibre extending longitudinally within the elongate body and having a distal end from which laser light is emitted for treatment. The distal end of the treatment fibre terminates at or projects distally from the convex contact surface and is supported laterally around by the surrounding solid material of the contact member. This treatment probe is used to treat glaucoma in particular.

A similar treatment probe is known from U.S. Pat. No. 10,292,868 B2, in which the handpiece ends in an end piece that tapers concavely in the longitudinal direction to the optical axis of the optical fiber and then increases concavely again. At the distal end, a contoured surface is formed as a contact surface, which is concave when viewed in a plane directed transversely to the optical axis and can thus be adapted to the curvature of the outer shape of the eye. Here, too, an exit end of the optical fiber ends in the centre of the concave contact surface and protrudes forward slightly beyond this contact surface. In particular, the concave contoured contact surface has a single radius of curvature, i.e. it is spherical in shape. In addition to the concave surface, a further contact to the eye is made by a rim placed on the limbus, which rim limits the contoured surface.

The handpiece with the convex contact surface according to EP 3 160 379 B1 allows a good gliding over the surface of the eye during surgery due to the small, rather punctiform contact with the eye, but can tilt easily on its own. The handpiece with the concave surface known from U.S. Pat. No. 10,292,868 B2 allows a more extensive and stable contact with the cornea of the eye, but is not quite as suitable for different eye sizes.

In these handpieces for glaucoma therapy, known from EP 3 160 379 B1 and U.S. Pat. No. 10,292,868 B2, the optical fiber is guided and held through a centrally located hole in the solid body of the applicator head and exits at the convex or concave contact surface. As a result, the optical fiber, which then touches down on the eye, is held laterally by the surrounding material of the applicator head in its central bore and cannot break off or be damaged and can nevertheless rest with its exit end directly against the cornea to avoid optical loss.

BRIEF SUMMARY OF THE INVENTION

An object of the present invention is to provide an eye treatment device, in particular for the treatment of glaucoma, with an alternative applicator head.

This object is solved according to an embodiment of the invention by the features of patent claim 1. Further embodiments and variants according to the invention result in particular from the dependent patent claims.

In one embodiment, the eye treatment device, which is in particular for use in glaucoma therapy, comprises a) at least one applicator head (or: instrument) for applying (or: utilizing, irradiating) laser light (or: laser radiation) into the eye, b)
  wherein the applicator head comprises at least one light guide with an exit end (or: outlet) for the laser light and a cavity with an opening enclosed (or: limited) by a contact ring for placement (or: resting) on the eye, c) wherein the light guide extends self-supporting and/or exposed within the cavity.

The contact ring enables stable, non-tilting positioning of the applicator head on the ocular surface, especially the cornea.

The cavity is preferably provided and formed for receiving treatment fluid, in particular lubricating fluid, on the ocular surface, the treatment fluid serving as a coolant for (or: for cooling of) the light guide exposed in the cavity.

In one embodiment, the light guide extends along a central axis at least in its end region up to the exit end. The contact ring preferably runs annularly, in particular circularly, around the central axis.

In a particularly advantageous embodiment, the contact ring extends (or: lies) substantially within a contact plane which is preferably directed perpendicular to the central axis.

The light guide is preferably an optical fiber and/or preferably has a diameter of 100 to 800 μm, in particular between about 500 and 700 μm.

In an advantageous embodiment, the exit end of the light guide protrudes (or: projects) from the cavity and/or in front of the contact ring or the contact plane by a protrusion (or: projecting length). This protrusion of the exit end of the light guide is preferably selected as 0.2 to 1.2 times, in particular between 0.4 and 0.8 times, the diameter of the light guide and/or between 0.1 mm and 0.8 mm, in particular between 0.3 mm and 0.6 mm.

In an advantageous embodiment, an inner diameter of the contact ring or the opening of the cavity is selected between 1.5 mm and 4 mm, in particular between 2.5 mm and 3.5 mm, and/or between 1.8 times and 40 times, in particular between three times and seven times, the diameter of the light guide.

In an advantageous embodiment, the applicator head has a bell wall (or: bell-shaped wall) that surrounds the cavity and extends to the contact ring that forms an end face of the bell wall. Preferably, the bell wall encircles the central axis. In one embodiment, an inner surface of the bell wall defining the cavity is concave with respect to the central axis.

In an advantageous further development, the applicator head has a support area adjacent to the cavity for supporting the light guide in the radial direction, wherein in particular a guide channel for the light guide is formed in the support area, the inner diameter of which is adapted to the diameter of the light guide. Following the support area, the applicator head can now have a further cavity on the side of the support area facing away from the cavity, wherein in particular the light guide is at least partially self-supporting and/or exposed in the further cavity and/or is held in a holding element which is fastened in the further cavity and which preferably projects on the other side into an interior of a hollow handpiece to which the applicator head is fastened.

In a particularly advantageous embodiment, an (axial) depth of the cavity from its proximal end or from the support area to the (distal) opening on the contact ring is selected as a function of the diameter D of the (distal) opening of the cavity or of the contact ring 21 as follows:

a) $D<a<2\,D$, in particular $0.3\,D<a<1.6\,D$ or $0.8\,D<a<1.3\,D$.

The light guide is suitably rounded at the exit end, in particular by melting by means of a laser or with the aid of a splicer.

In a preferred embodiment, the contact ring is rounded in profile or in its cross-section or contour, in particular with a convex curvature with a radius of curvature in a range from 0.1 mm to 0.4 mm, in particular at or below 0.2 mm The applicator head can preferably consist entirely or at least in the area of the contact ring and preferably also of the bell wall of thermoplastic material.

In a particularly advantageous embodiment, the contact ring is now rounded in profile or in its cross-section or in its contour by thermal forming of the plastic material, which is carried out or has been carried out with the aid of a hot gas stream, in particular a hot air stream, wherein in particular the treatment temperature of the hot gas or the hot air is selected as a function of the softening temperature or the melting temperature of the plastic used and is selected in particular between 130° C. and 200° C. and/or the contact ring (with the applicator head) is rotated in the hot gas stream.

In an embodiment a method for shaping the contact ring of the eye treatment device, in which the applicator head consists entirely or at least in the region of the contact ring, and preferably also of the bell wall (22), of thermoplastic material, comprises the step of exposing the contact ring to hot gas flow, in particular a hot air stream, for rounding the profile or the cross-section or the contour of the contact ring by thermal reshaping of the thermoplastic material, wherein particular the treatment temperature of the hot gas or the hot air is selected depending on the softening temperature or the melting temperature of the thermoplastic material used.

The treatment temperature is preferably selected between 130° C. and 200° C.

The contact ring is preferably rotated in the hot gas stream.

BRIEF DESCRIPTION OF THE DRAWINGS

The invention will be further explained below with reference to exemplary embodiments. Reference is also made to the drawings, which show schematically in each case.

FIG. 2 a side view of an eye treatment device with an applicator head,

FIG. 3 the eye treatment device according to FIG. 2 in a longitudinal section, FIG. 4 the applicator head of the eye treatment device according to FIG. 3 in an enlarged view and only in the front part in longitudinal section, FIG. 5 another embodiment of an applicator head in the front part in a longitudinal section and FIG. 6 a further embodiment of an applicator head in the front part in a longitudinal section.

Corresponding parts and entities are marked with the same reference signs in the FIGS. 1 to 6.

DETAILED DESCRIPTION

Figure 1:
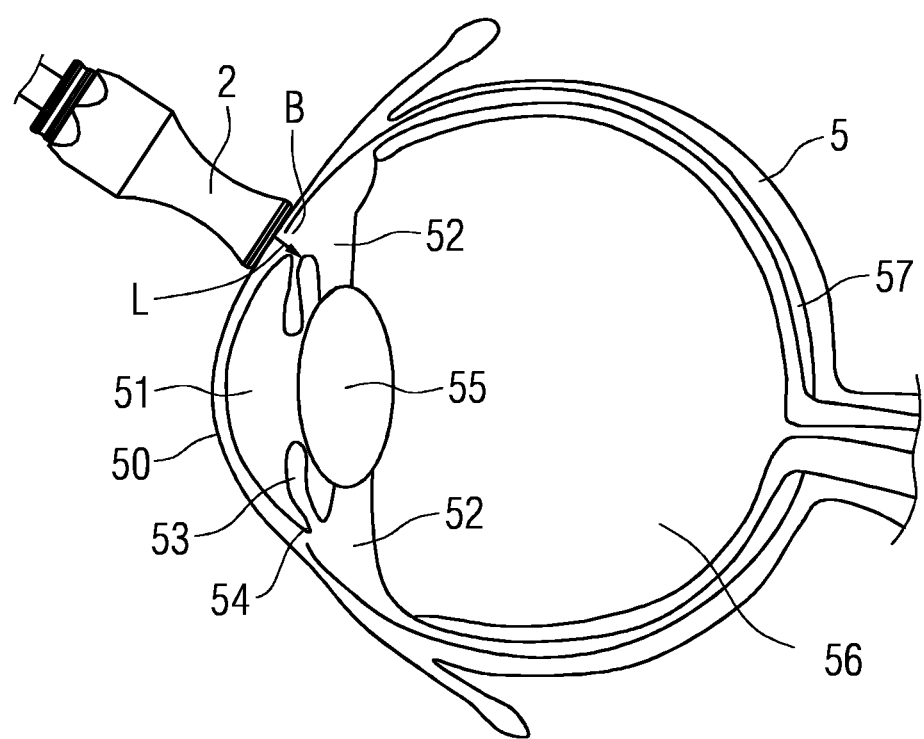
FIG. 1 an applicator head placed on an eye from the outside.

FIG. 1 shows an eye 5 with cornea 50, anterior eye chamber 51 filled with ocular fluid, ciliary muscle 52, iris 53, trabecular meshwork 54, lens 55 held by the ciliary muscle 52, vitreous body 56 and the retina 57 arranged in the posterior eye and further parts not designated or not shown. In the region of the cornea 50, in particular in the vicinity of the trabecular meshwork 54 and/or the ciliary muscle 52, an applicator head 2 is placed on the cornea 50 from the outside with a contact ring described in more detail below and emits laser light L into a treatment zone B. This treatment zone B is in particular a region of the ciliary muscle 52 or the trabecular meshwork 54, in order to carry out a glaucoma treatment. Typically, in such a treatment, the applicator head 2 is guided around along an annular or arcuate movement over the cornea 50, in particular at the edge of the iris 53, whereby individual disjoint treatment zones B can be treated or a contiguous treatment zone B can be treated.

FIGS. 2 and 3 show an applicator head 2 as shown in FIG. 1 and additional parts of an eye treatment device adjoining the applicator head 2. In the longitudinal section shown in FIG. 3 and in the enlarged view of FIG. 4, further details of the applicator head 2 can also be seen. FIGS. 5 and 6 show variants of the applicator head 2, but the basic structure described below is the same.

Figure 4:
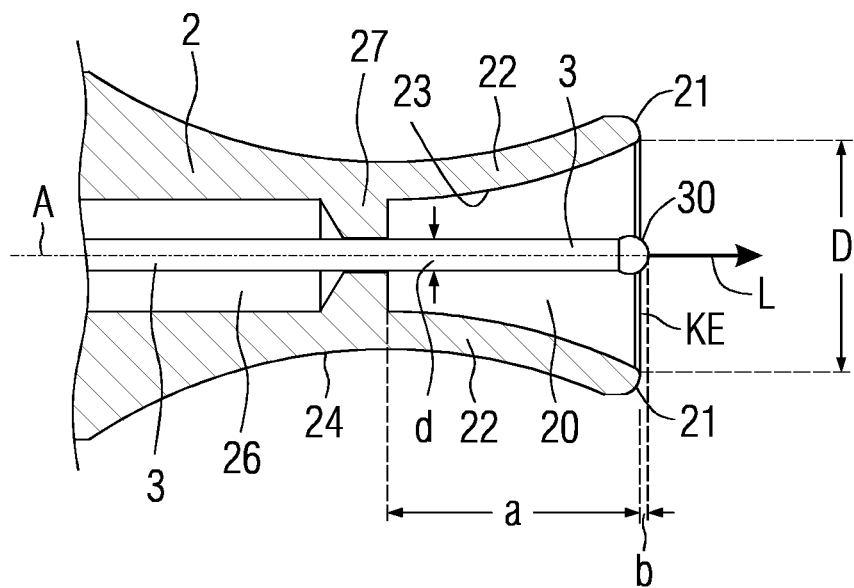
Figure 5:
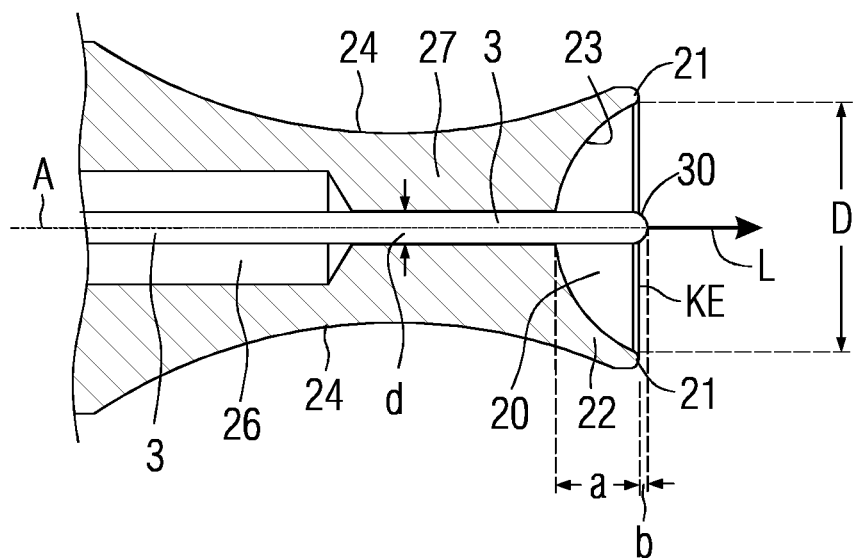
Figure 6:
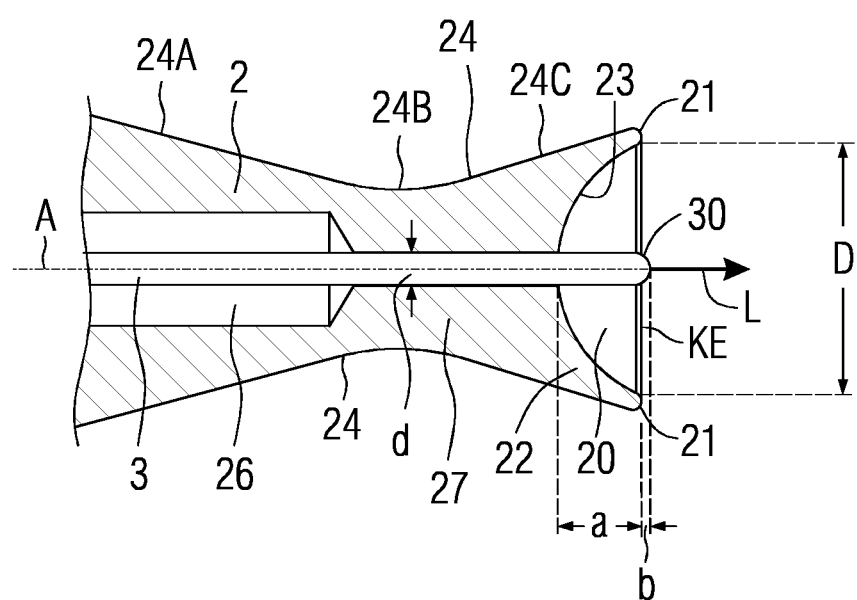

As can be seen in particular in FIGS. 4 to 6, the applicator head 2 has a contact ring 21 at its distal end as seen axially with respect to the central axis A, with which the applicator head 2 comes into contact with the ocular surface, in particular the cornea 50 as shown in FIG. 1, and is placed on the ocular surface.

The contact ring 21 runs annularly, i.e. along a closed contour or as a topologically closed ring structure, around the central axis A and is in particular circular or annular.

The contact ring 21 forms a, compared to the known glaucoma treatment probes mentioned at the beginning, smaller, in particular approximately linear, contact ring surface, with which the applicator head 2 rests on the surface of the eye during use. The support of the applicator head 2 on the eye via the contact ring 21 is very stable and tilt-resistant.

Preferably, the contact ring 21 itself is somewhat rounded or convex in profile or cross-section in order to make the contact of the resting contact ring surface with the ocular surface even smaller or even more linear and also to avoid damage to the cornea or ocular surface by too sharp edges.

Typically, the convex curvature of the rounded profile or cross-section of the contact ring 21 is in a range of 0.1 mm to 0.4 mm, in particular 0.2 mm, for radii of curvature.

In an advantageous embodiment, the applicator head 2 consists entirely or at least in the region of the contact ring 21 and the bell wall 22 of a thermoplastic material.

Here, in a particularly advantageous embodiment, the contact ring 21 of the applicator head moulded part, produced for example by injection moulding, can be treated or shaped by a method involving exposing the contact ring 21 to a hot gas flow, in particular a hot air flow, wherein the moulded part can be rotated in particular in the gas or air flow. This treatment or shaping method causes the contours on the contact ring 21 to round off or acquire larger radii of curvature due to the thermal reshaping of the plastic material. The treatment temperature of the hot gas or hot air depends on the softening temperature and also the melting temperature of the plastic material used and, without limiting generality, is selected in particular between 130° C. and 200° C.

The maximum thickness of the wall at the contact ring 21 is in particular selected to be smaller than the diameter d of the light guide.

Particularly advantageous is an embodiment as shown in FIGS. 4 to 6, in which the contact ring 21 and its contact ring surface extend substantially within a contact plane KE. The contact plane KE is a geometric plane which is preferably perpendicular to the central axis A. Hence, the contact ring 21 and its contact ring surface and thus the contact surface of the applicator head 2 preferably lie in one plane.

This results in a circumferential annular support surface lying in a plane KE and allows the applicator head 2, which is usually hand-held, to be supported on the eye in a very stable, tilt-proof manner.

In principle, however, it is also possible to form the contact ring 21 along a slightly curved, in particular concave or convex, surface instead of a contact plane KE, in particular in adaptation to the shape of the eye.

The contact ring 21 generally forms, as also shown in FIGS. 4 to 6, the distal end region or the distal end face of a bell-shaped wall or bell wall 22, which encircles the central axis A in a closed manner.

The bell wall 22 encloses a cavity 20, the distal opening of which is bound or enclosed by the contact ring 21. The contact ring 21 forms an end face of the bell wall 22.

The inner surface 23 of the bell wall 22 bounding the cavity 20 is concave in FIG. 4 with respect to the central axis A and convex in FIGS. 5 and 6. With respect to the opening in the contact ring 21 or the contact plane KE. The bell wall 22 is concave in FIG. 4 with respect to the central axis A and convex in FIGS. 5 and 6.

An inner diameter of the contact ring 21 or the distal opening of the cavity 20 is denoted by D and is typically between 1.5 mm and 4 mm, in particular between 2.5 mm and 3.5 mm.

Within the cavity 20 enclosed by the bell wall 22, an light guide 3 runs, preferably centrally or centrally along the central axis A, which thus then corresponds to the optical axis of the light guide 3 and of the laser light L propagating therein. The light guide 3 is in particular an optical fiber with a thickness or diameter d of typically 100 to 800 μm, for example about 500 to 700 μm. The light guide 3 ends at a distal end which forms an exit end 30 for the laser light L.

The diameter D of the contact ring 21 or of the distal opening of the cavity 20 is chosen in particular as a function of the diameter d of the light guide 3 as follows: $1.8\,d<D<40\,d$, preferably $3\,d<D<7\,d$.

In the embodiment examples shown, the applicator head 2 has a continuous outer wall 28 running axially to the central axis A (only shown completely in FIG. 3, partially in FIGS. 4 to 6), within which at least one further cavity 26 is also formed in addition to the cavity 20, which the outer wall 28 surrounds in its front region as a bell wall 22. The two cavities 20 and 26 are arranged axially offset from each other and separated from each other by a support area 27 for the light guide 3. While the diameters of the cavities 20 and 26 measured perpendicular to the axis A are significantly larger than the diameter d of the light guide 3 to expose it, a guide channel is formed in the support area 27, the inner diameter of which is adapted to the diameter of the light guide 3.

As a result, the light guide 3 is supported and held all around or in the radial direction by the support area 27 and the end region of the light guide 3 projecting beyond the support area 27 can run self-supporting (or: unsupported or contactless) and/or exposed within the cavity 20 and end self-supporting at the free exit end 30 without surrounding walls.

An axial dimension or depth of the cavity 20 from its proximal end or from the support area 27 to the distal opening at the contact ring 21 is denoted by a and here also corresponds to the length of the free end area of the light guide 3 in the cavity 20.

The axial depth (a) of the cavity 20 is generally chosen as a function of the diameter D of the distal opening of the cavity 20 or of the contact ring 21 as follows: $0.1\,D<a<2\,D$, in particular $0.3\,D<a<1.6\,D$ or $0.8\,D<a<1.3\,D$.

In the exemplary embodiment of FIG. 4, the depth (a) is approximately 1.1 D. In the exemplary embodiment of FIGS. 5 and 6, the depth (a) is selected to be smaller than the diameter D, for example approximately ⅓ D. Here, the support area 27 is preferably also longer, i.e. the light guide 3 is supported more than in FIG. 4.

Due to the correspondingly deep cavity 20, the applicator head 2 according to the invention has a lower mass at the distal end compared to the known applicator heads of the prior art described at the beginning, which are solidly formed at the contact surface and have a continuous contact surface and a continuous support channel for the light guide up to its exit end projecting in front of the contact surface.

Furthermore, the optical fiber or the light guide 3, due to the non-contact arrangement in the cavity 20 and it being exposed and/or self-supporting in the cavity 20 up to the exit end 30 according to the invention, is thermally better cooled by the liquid medium on the ocular surface, in particular cornea 50, which accumulates or is trapped in the cavity 20 during the treatment. Such liquid medium is in particular a liquid lubricant such as Methocel® used during the operation. The cavity 20 thus advantageously serves to receive or collect liquid on the ocular surface as a coolant for the light guide 3.

In a preferred embodiment, as also shown in FIGS. 4 to 6, the exit end 30 of the light guide protrudes outwards from the cavity 20 of the applicator head 2 or over the contact surface of its contact ring 21, in particular the contact plane KE. This ensures a safe contact of the exit end 30 to the eye surface, in particular cornea 50, even without being pressed in under pressure via the contact ring 21, and any burns to the eye tissue are avoided.

The dimension axial to the axis A or the protrusion of the part of the light guide 3 protruding from the cavity 20 at the exit end 30 is denoted by b in FIGS. 4 to 6 and corresponds in these embodiment examples according to FIGS. 4 to 6 to the maximum distance of the exit end 30 of the light guide 3 from the contact plane KE.

This dimension or protrusion b, by which the exit end 30 of the light guide 3 protrudes from the cavity 20, is chosen in particular between 0.2 d to 1.2 d, in particular between 0.4 d and 0.8 d, of the diameter d of the light guide 3 and/or between 0.1 mm and 0.8 mm, in particular between 0.3 mm and 0.6 mm.

The axial distance of the exit end 30 of the light guide 3 from the support area 27 or the total length of the self-supporting end area of the light guide 3 corresponds to the sum a+b.

The exit end 30 of the light guide 3 lies directly on the cornea 50 as a result of the protrusion. Direct contact of the exit end 30 of the light guide 3 is advantageous because it prevents burns to the eye.

In an embodiment not shown, however, the exit end 30 of the light guide 3 can also be flush with the contact plane KE or, more generally, the contact ring 21, or even slightly recessed into the cavity 20. In this case, the applicator head 2 would have to be pressed slightly against and into the cornea 50 by the person treating the patient via the contact ring 21 in order to ensure contact of the exit end 30 of the light guide 3 with the cornea 50.

The light guide 3 is preferably rounded at the exit end 30 to support smooth gliding on the ocular surface. The rounding of the exit end 30 of the light guide 3 can be done, for example, by melting the optical fibre of the light guide at the exit end 30 by means of a laser, whereby the rounded exit end 30 can obtain a partially approximately spherical shape, also possibly with an extension greater than the diameter d of the light guide 3 as shown in FIG. 4, or also with the aid of a splicer, whereby a rounding with a thickness smaller than the diameter d of the light guide 3 usually results, as shown in FIGS. 5 and 6.

The outer surface 24 of the wall of the applicator head 2 runs in a concave curved manner in the embodiment example shown in FIGS. 2 and 3, the concave outer surface 24 begins at a particularly cylindrical thicker region of the applicator head 2 to which the handpiece 6 is attached and, after tapering approximately in the region of the support area 27, widens again in a bell-shaped manner in the region in which the bell wall 22 encloses the cavity 2.

On the applicator head 2, as can be seen in FIGS. 2 and 3, a retaining element 4 is fixed in the central cavity 26 at the proximal end facing away from the distal end with the contact ring 21, in particular by means of threads not further described and/or bonding. The retaining element 4 holds the light guide 3 in the radial direction in an inner guide channel 41 adapted to the diameter d of the light guide 3. On the other side, the retaining element 4 projects into an interior 61 of a hollow handpiece 6, which in turn is attached at its distal end to the outside of the applicator head 2, for example again by a corresponding screw connection and/or adhesive bond. On its outer surface, the handpiece 6 has a gripping area 60 where a person treating the patient can grip the handpiece 6 and thus the entire device.

An adapter 7 with an inner cavity 71 is attached to the proximal end of the handpiece 6, in particular again by a screw connection and/or glue bonding. A hollow bolt-shaped extension 70 projects into a sleeve 9 and is connected to it, for example, again by means of an adhesive bond. Inside the sleeve 9 runs a tube 8 which encloses the light guide 3 and projects with its end into the cavity 71 in the adapter 7. The light guide 3 preferably runs continuously centrally along or on the central axis A through the tube 8 in the sleeve 9 and then through the adapter 7, then through the handpiece 6 and through the guide channel 41 in the holding element 4, and then in the applicator head 2 through the rear cavity 26, the support area 27 and finally through the front cavity 20 to its distal exit end 30 on the contact ring 21.

The components shown are formed and aligned along a central axis A and can, for example, be formed essentially symmetrical around this central axis A and/or be rigid or also partially flexible. However, curved arrangements or arrangements at angles are also possible. The parts used are preferably glued together after being screwed or plugged together.

In the direction from the proximal to the distal end, which usually corresponds to the direction of insertion for the light guide 3, through which the light guide is thus passed with its exit end 30, from left to right in FIGS. 2 and 3, at least the components retaining element 4 and support area 27 have funnel-shaped insertion aids so that the light guide 3 can be threaded through more easily and without damage.

In the preferred embodiments shown in FIGS. 1 to 6, the outer wall 28 of the applicator head 2 has, at least in a partial region, an outer surface 24 which tapers axially towards the central axis A and widens again. After tapering, the outer surface 24 widens again approximately in the region of the support area 27 and then forms the bell wall 22 which encloses the cavity 20. Towards the proximal end or towards the handpiece 6, the outer wall 28 can also have, for example, a cylindrical outer surface following the outer surface 24 (cf. FIGS. 2 and 3).

In the embodiments shown in FIGS. 1 to 5, the tapering and re-widening outer surface 24 has a concave curvature throughout.

In FIG. 6, in contrast to FIG. 5, the tapering and then widening outer surface 24 of the applicator head 2 is formed by a substantially conically tapering conical surface 24A, a cylindrical surface 24B forming the tapered or thinnest part, and a conically widening conical surface 24C again towards the distal end where the annular surface 21 is located. The taper of the applicator head in the axial direction or the concave or otherwise decreasing and then increasing outer surface 24 of the applicator head 2 has the advantage that the field of vision of the person performing the operation is expanded or improved.

Laser light L within the meaning of the present application is understood to be not only laser radiation in the visible spectrum but also in the infrared spectrum and, in general, any laser radiation generated by means of a laser which is suitable for treatment in the eye, in particular the therapy of glaucoma.

The laser light used for the treatment of glaucoma in the eye treatment device is preferably pulsed with wavelengths in the range at the end of the optical spectrum or the near infrared spectrum, in particular around 810 nm and pulse durations of 0.08 ms to 5 ms and is generated by a laser source which is not shown and is optically coupled to the light guide 3, in particular directly or via further light guides.

LIST OF REFERENCE SIGNS 2 applicator head
3 light guide
4 retaining element
5 eye
6 hand piece
7 adapter
8 tube
9 sleeve
20 cavity
21 contact ring
22 bell wall
23 inner surface
24 outer surface 24A conical surface
24B cylindrical surface
24 cone surface
26 cavity
27 support area
28 wall
30 exit end
50 cornea
51 anterior eye chamber
52 ciliary muscle
53 iris
54 trabecular meshwork
55 lens
56 vitreous body
57 retina
60 gripping area
61 interior
A central axis
B treatment zone
D diameter (contact ring)
a depth, or "depth (a)"
d diameter (light guide)
b protrusion
KE contact level
L laser light

I claim:

1. An eye treatment device for use in glaucoma therapy, comprising:
   a) at least one applicator head for applying laser light (L) into an eye;
   b) wherein the applicator head comprises:
   b1) at least one light guide with an exit end for the laser light (L) at a distal end of the light guide;
   b2) a cavity with an opening enclosed by a contact ring for placement on the eye, the cavity having an inner surface, and
   b3) the light guide extending self-supporting and exposed within the cavity, wherein the inner surface of the cavity is spaced apart from the light guide;
   b4) wherein the cavity is configured to receive and collect treatment fluid on an ocular surface of the eye, the treatment fluid being accumulated in the cavity to cool the light guide exposed in the cavity,
   b5) wherein an inner diameter of the contact ring of the cavity is selected between three times and 40 times the diameter of the light guide;
   wherein an inner diameter (D) of the contact ring or of the opening of the cavity is selected between one of (i): 1.5 mm and 4 mm, (ii) between 2.5 mm and 3.5 mm, or (iii) between three times and seven times, the diameter (d) of the light guide.

2. The eye treatment device according to claim 1, wherein the light guide extends along a central axis (A) at the distal end up to the exit end and the contact ring runs in an annular shape around the central axis (A).

3. The eye treatment device according to claim 1, wherein the contact ring extends substantially within a contact plane (KE), which is directed perpendicularly to the central axis (A).

4. The eye treatment device according to claim 1, wherein the light guide is an optical fiber and has a diameter (d) of 100 to 800 μm.

5. The eye treatment device according to claim 1, wherein the exit end of the light guide protrudes from the cavity or in front of the contact ring or the contact plane (KE) by a protrusion (b).

6. The eye treatment device according to claim 5, wherein:
   the protrusion (b) of the exit end of the light guide corresponds to the product of between 0.2 d and 1.2 d, wherein d is a diameter (d) of the light guide; and
   the diameter (d) of the light guide is chosen between 0.1 mm and 0.8 mm.

7. The eye treatment device according to claim 1, wherein the applicator head comprises a bell wall enclosing the cavity and extending to the contact ring forming an end face of the bell wall.

8. The eye treatment device according to claim 7, wherein:
   the bell wall encircles the central axis (A); and/or
   the inner surface of the cavity is an inner surface of the bell wall, wherein the inner surface of the bell wall delimits the cavity and is concave with respect to the central axis (A).

9. The eye treatment device according to claim 1, wherein:
   the applicator head has, adjoining the cavity, a support area for supporting the light guide in the radial direction; and
   a guide channel for the light guide is formed in the support area, the inside diameter of which guide channel contacts and supports the light guide.

10. The eye treatment device according to claim 9, wherein:
    the applicator head has a further cavity adjoining the support area proximal to the support area; and
    the light guide is at least partially spaced apart from an inner surface of the further cavity and is held in a holding element which is fastened in the further cavity and which projects opposite the cavity into an interior of a hollow handpiece to which the applicator head is fastened.

11. The eye treatment device according to claim 1, wherein a depth a of the cavity from its proximal end or from the support area to the opening at the contact ring is selected as a function of the diameter d of the opening of the cavity or of the contact ring 21 as follows: 0.1 d<a<2 d.

12. The eye treatment device according to claim 1, wherein the contact ring is rounded in profile or in its cross-section or contour, and has a convex curvature having a radius of curvature in a range from 0.1 mm to 0.4 mm.

13. The eye treatment device according to claim 12, wherein:
    the applicator head comprises a bell wall enclosing the cavity and extending to the contact ring forming an end face of the bell wall;
    the applicator head consists entirely or at least in the region of the contact ring, and also of the bell wall, of thermoplastic material;
    the contact ring is rounded in profile or in its cross-section or in its contour by thermal reshaping of the thermoplastic material with the aid of a hot gas flow, in particular a hot air stream;
    a treatment temperature of the hot gas or the hot air is selected depending on the softening temperature or the melting temperature of the thermoplastic material used and in particular is selected between 130° C. and 200° C.; and/or
    the contact ring is rotated in the hot gas stream.

14. The eye treatment device according to claim 1, wherein the light guide is rounded at the exit end, in particular by melting by a laser or with the aid of a splicer.

15. A method for shaping a contact ring of an applicator head of an eye treatment device for use in glaucoma therapy, according to claim 1, wherein the contact ring encloses an opening of a cavity within the applicator head and is to be placed on the eye and wherein the applicator head consists entirely or at least in the region of the contact ring of thermoplastic material, the method comprising the step of:

shaping the contact ring by exposing the contact ring to hot gas flow comprising a hot air stream, for rounding the profile or the cross-section or the contour of the contact ring by thermal reshaping of the thermoplastic material, wherein:

the treatment temperature of the hot gas or the hot air is selected depending on the softening temperature or the melting temperature of the thermoplastic material used;

the treatment temperature is selected between 130° C. and 200° C.; and the contact ring is rotated in the hot gas stream.

16. The eye treatment device according to claim 1, wherein the light guide is an optical fiber and has a diameter (d) of between about 500 and 700 μm.

17. An eye treatment device for use in glaucoma therapy, comprising:

a) at least one applicator head for applying laser light (L) into an eye;

b) wherein the applicator head comprises:

b1) at least one light guide with an exit end for the laser light (L) at a distal end of the light guide;

b2) a cavity with an opening enclosed by a contact ring for placement on the eye, the cavity having an inner surface, and b3) a bell wall enclosing the cavity and extending to the contact ring forming an end face of the bell wall, wherein the inner surface of the cavity is an inner surface of the bell wall, b4) the light guide extending self-supporting and exposed within the cavity, wherein the inner surface of the cavity is spaced apart from the light guide;

b5) wherein the cavity is configured to receive and collect treatment fluid on an ocular surface of the eye, the treatment fluid being accumulated in the cavity, and cooling the light guide exposed in the cavity, b6) wherein an inner diameter of the contact ring of the cavity is selected between three times and 40 times the diameter of the light guide;

wherein:

the applicator head has, adjoining the cavity, a support area for supporting the light guide in the radial direction;

a guide channel for the light guide is formed in the support area, the inside diameter of which guide channel contacts and supports the light guide;

the applicator head has a further cavity adjoining the support area proximal to the support area; and the light guide is at least partially spaced apart from an inner surface of the further cavity and is held in a holding element which is fastened in the further cavity and which projects opposite the cavity into an interior of a hollow handpiece to which the applicator head is fastened.

* * * * *